United States Patent
Wang et al.

(10) Patent No.: US 7,781,581 B2
(45) Date of Patent: Aug. 24, 2010

(54) PROCESS FOR THE PREPARATION OF 5-AMINO-3H-THIAZOLO[4,5-D]PYRIMIDIN-2-ONE

(75) Inventors: Tingman Wang, San Diego, CA (US); John S. Ng, Oak Park, CA (US); Stephen E. Webber, San Diego, CA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 482 days.

(21) Appl. No.: 11/601,719

(22) Filed: Nov. 20, 2006

(65) Prior Publication Data

US 2007/0117979 A1 May 24, 2007

Related U.S. Application Data

(60) Provisional application No. 60/738,055, filed on Nov. 21, 2005.

(51) Int. Cl.
C07D 487/04 (2006.01)
(52) U.S. Cl. ..................................................... 544/255
(58) Field of Classification Search .................. 544/255
See application file for complete search history.

(56) References Cited

U.S. PATENT DOCUMENTS

| | | | |
|---|---|---|---|
| 4,539,205 A | 9/1985 | Goodman et al. |
| 4,643,992 A | 2/1987 | Goodman et al. |
| 4,746,651 A | 5/1988 | Goodman |
| 4,880,784 A | 11/1989 | Robins et al. |
| 5,011,828 A | 4/1991 | Goodman et al. |
| 5,041,426 A | 8/1991 | Robins et al. |
| 5,041,542 A | 8/1991 | Robins et al. |
| 5,166,141 A | 11/1992 | Goodman et al. |
| 5,248,672 A | 9/1993 | Townsend et al. |
| 5,395,937 A | 3/1995 | Nikolaides et al. |
| 5,424,295 A | 6/1995 | Krenitsky et al. |
| 5,446,045 A | 8/1995 | Revankar et al. |
| 5,492,897 A | 2/1996 | Krenitsky et al. |
| 5,496,816 A | 3/1996 | Blizzard et al. |
| 5,821,236 A | 10/1998 | Krenitsky et al. |
| 5,994,321 A | 11/1999 | Lewis et al. |
| 6,028,076 A | 2/2000 | Hirota et al. |
| 6,329,381 B1 | 12/2001 | Kurimoto et al. |
| 6,376,501 B1 | 4/2002 | Isobe et al. |
| 6,479,463 B1 | 11/2002 | Wang et al. |
| 6,509,320 B1 | 1/2003 | Wang et al. |
| 6,566,344 B1 | 5/2003 | Gosselin et al. |
| 6,924,271 B2 | 8/2005 | Averett et al. |
| 2002/0058635 A1 | 5/2002 | Averett |
| 2002/0173655 A1 | 11/2002 | Dellaria et al. |
| 2003/0065005 A1 | 4/2003 | Charles et al. |
| 2003/0100764 A1 | 5/2003 | Bonk et al. |
| 2003/0162806 A1 | 8/2003 | Dellaria et al. |
| 2003/0176458 A1 | 9/2003 | Dellaria et al. |
| 2003/0186949 A1 | 10/2003 | Dellaria et al. |
| 2003/0195209 A1 | 10/2003 | Dellaria et al. |
| 2003/0199461 A1 | 10/2003 | Averett et al. |
| 2004/0063658 A1 | 4/2004 | Roberts et al. |
| 2005/0004144 A1 | 1/2005 | Carson et al. |
| 2005/0054590 A1 | 3/2005 | Averett |
| 2005/0070556 A1 | 3/2005 | Averett et al. |
| 2005/0182001 A1 | 8/2005 | Averett et al. |
| 2006/0160830 A1 | 7/2006 | Webber et al. |
| 2008/0020989 A1 | 1/2008 | Haley et al. |
| 2008/0032999 A1 | 2/2008 | Haley et al. |

FOREIGN PATENT DOCUMENTS

| | | |
|---|---|---|
| EP | 0882727 | 12/1998 |
| EP | 1035123 | 9/2000 |
| EP | 1043021 | 10/2000 |
| EP | 1219622 A2 | 7/2002 |
| EP | 1386923 | 2/2004 |
| WO | WO-89/05649 | 6/1989 |
| WO | WO-92/16215 A1 | 10/1992 |
| WO | WO-94/07904 | 4/1994 |
| WO | WO-94/17043 | 8/1994 |
| WO | WO-94/17090 A1 | 8/1994 |
| WO | WO-98/17279 | 4/1998 |
| WO | WO-03/045968 | 6/2003 |
| WO | WO-2006044775 A2 | 4/2006 |

(Continued)

OTHER PUBLICATIONS

Nagahara et. al. (J. Med. Chem., 1990, 33, 407-415).*

(Continued)

*Primary Examiner*—Susanna Moore
(74) *Attorney, Agent, or Firm*—Connolly Bove Lodge & Hutz LLP

(57) ABSTRACT

The present invention relates to a process for the preparation of 5-amino-3H-thiazolo[4,5-d]pyrimidin-2-one

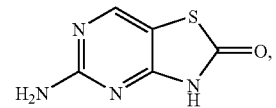

which is a useful intermediate in the preparation of certain thiazolo[4,5-d]pyrimidine nucleosides. The process comprises halogenating 2,4-diaminopyrimidine to form 2,4-diamino-5-halo-pyrimidine and then cyclocondensing the 2,4-diamino-5-halo-pyrimidine to form 5-amino-3H-thiazolo[4,5-d]pyrimidin-2-thione. The 5-amino-3H-thiazolo[4,5-d]pyrimidin-2-thione is then oxidized to afford the 5-amino-3H-thiazolo[4,5-d]pyrimidin-2-one.

16 Claims, No Drawings

FOREIGN PATENT DOCUMENTS

WO WO-2006122156 A2 11/2006

OTHER PUBLICATIONS

Uhrich (Science of Synthesis, 2002, 11, pp. 835-912).*
Baker et. al. (J. Chem. Soc. C, 1970, pp. 2478-2484).*
U.S. Appl. No. 12/015,821, Averett.
U.S. Appl. No. 11/873,202, Kucera.
Akira, "Mammalian Toll-like receptors", Current Opinion, 2003, 15: 5-11.
Akira, "Toll-Like Receptor Signalling", Immunology, 2004, 4:499-511.
Alexander et al., "(Acyloxy)alkyl Carbamates as Novel Bioreversible Prodrugs for Amines: Increased Permeation through Biological Membranes", J. Med. Chem., 1988, 31:318-322.
Applequist et al., "Variable expression of Toll-like receptor in murine innate and adaptive immune cell lines", Int. Immunol., 2002, 14(9):1065-74.
Barrio et al., "Regioselective Fluorination of Substituted Guanines with Dilute $F_2$: A Facile Entry to 8-Fluoroguanine Derivatives", J. Org. Chem., 1996, 61:6084-6085.
Bottcher et al., "Differential regulation of Toll-like receptor mRNAs in experimental murine central nervous system infections", Neurosci. Lett., 2003, 344(1):17-20.
Bruno et al., "Mouse pre-immunocytes as non-proliferating multipotent precursors of macrophages, interferon-producing cells, $CD8\alpha^+$ and $CD8\alpha^-$ dendritic cells", Eur. J. Immunol., 2001, 31(11):3403-12.
Chuang et al., "Cloning and charactericsation of a sub-family of human Toll-like receptors: hTLR7, hTLR8 and hTLR9", Eur. Cytokine Netw., Sep. 2000, 11(3):372-8.
Daskalov et al., Synthesis and Properties of O6-Substituted Guanosine Derivatives, Bull. Chem. Soc. Jpn., 54(10:3076-3083 (1981).
Diebold et al, "Innate antiviral responses by means of TLR7-mediated recognition of single-stranded RNA", Science, 2004, 303(5663):1481-2, abstract.
Doxsee et al, "The Immune Response Modifier and Toll-like Receptor 7 Agonist S-27609 Selectively Induces IL-12 and TNF-α Production in $CD11c^+CD11b^+CD8^-$ Dendritic Cells", J. Immunol., 2003, 171(3):1156-63).
Du et al., Eur. Cytokine Netw., 2000, 11(3), 362-71.
Edwards et al., "Toll-like receptor expression in murine DC subsets: lack of TLR7 expression by $CD8\alpha^+$ DC correlates with unresponsiveness to imidazoquinolines", Eur. J. Immunol., 2003, 33(4):827-33.
Fan et al., "Pyrimidines. 24. Analogues and Derivatives of 2-Amino-5-bromo-6-phenyl-4(3H)-pyrimidinone (ABPP)", J. Heterocyclic Chem., Nov. 1993, 30:1273-1276.
Fathi et al., "Synthesis of 6-Substituted 2'-Deoxyguanosine Derivatives Using Trifluoroacetic Anhydride in Pyridine", Tetrahedron Letters, 31(3):319-322 (1990).
Fried, et al., "5-Substituted 2-Amino-6-phenyl-4(3H)-pyrimidinones. Antiviral- and Interferon-Inducing Agents", J. Med. Chem., 1980, 23:237-239.
Fujiwara et al., "Synthesis and Bioactivities of Novel Piperidylpyrimidine Derivatives: Inhibitors of Tumor Necrosis Factor-Alpha Production", Bioorg. Med. Chem. Lett., 2000, 10(12):1317-1320.
Furneaux et al., "Improved Syntheses of 3H,5H-Pyrrolo[3,2-d]pyrimidines", J. Org. Chem., 64(22), 8411-8412 (1999).
Gangwar et al., "Synthesis of a Novel Esterase-Sensitive Cyclic Prodrug of a Hexapeptide Using an (Acyloxy)alkoxy Promoiety)", J. Org. Chem., 1997, 62:1356-1362.
Gibson et al., "Plasmacytoid dendritic cells produce cytokines and mature in response to the TLR7 agonists, imiquimod and resiquimod", Cell Immunol., 2002, 218(1-2):74-86.
Girgis et al., "Direct C-Flycosylation of Guanine Analogues: The Synthesis and Antiviral Activity of Certain 7- and 9-Deazaguanine C-Nucleosides", J. Med. Chem., 1990, 33:2750-2755.

Goodman, "Role of Salvage and Phosphorylation in the Immunostimulatory Activity of C8-Substituted Guanine Ribonucleosides", J. Immunol., 14(7):2394-2399 (1988).
Hall et al., "Aldehyde Oxidase from Rabbit Liver: Specificity Toward Purines and Their Analogs", Archives of Biochemistry and Biophysics, 25(1):36-46 (1986).
Heil et al., "The Toll-like receptor 7 (TLR7)-specific stimulus loxoribine uncovers a strong relationship within the TLR7, 8 and 9 subfamily", Eur. J. Immunol., 2003, 33(11):2987-97.
Hemmi et al., "Small anti-viral compounds activate immune cells via the TLR7 MyD88-dependent signaling pathway", Nat. Immunol., 2002, 3(2):196-200.
Henry et al., "Synthesis and Broad-Spectrum Antiviral Activity of 7,8-Dihydro-7-methyl-8-thioxoguanosine", J. Med. Chem., 1990, 33:2127-2130.
Hirota et al., "Discovery of 8-Hydroxyadenines as a Novel Type of Interferon Inducer", J. Med. Chem., 2002, 45:5419-5422.
Horng et al., "The adaptor molecule TIRAP provides signaling specificity for Toll-like receptors", Nature, 2002, 420(6913):329-333.
Hornung et al., "Quantitative Expression of Toll-Like Receptor 1-10 mRNA in Cellular Subsets of Human Peripheral Blood Mononuclear Cells and Sensitivity to CpG Oligodeoxynucleotides", J. Immunol., 2002, 168(9):4531-4537.
International Search Report (PCT/US2004/028236) dated Mar. 14, 2005.
International Search Report (PCT/US02/38001) dated Mar. 18, 2003.
Isobe et al, "Synthesis and Structure-Activity Relationships of 2-Substituted-8-hydroxyadenin Derivatives as Orally Available Interferon Inducers without Emetic Side Effects", Bioorganic & Medicinal Chemistry, 2003, 11:3641-3647.
Ito et al., "Roles of Toll-Like Receptors in Natural Interferon-Producing Cells as Sensors in Immune Surveillance", Hum. Immunol., 2002, 63(12):1120-1125.
Jarrossay, "Specialization and complementarity in microbial molecule recognition by human myeloid and plasmacytoid dendritic cells", Eur. J. Immunol., 2001, 31(11):3388-3393.
Jones et al., "Di- and Triester Prodrugs of the Varicella-Zoster Antiviral Agent 6-Methoxypurine Arabinoside", J. Med. Chem., 35(1):56-63 (1992).
Jurk et al., "Human TLR7 or TLR8 independently confer responsiveness to the antiviral compound R-848", Nat. Immunol., 2002, 3(6):499.
Kini et al., "Synthesis and Antiviral Activity of Certain Guanosine Analogues in the Thiazolo[4,5-d]pyrimidine Ring System", J. Med. Chem., 1991, 34:3006-3010.
Krasny et al., "Metabolism and Pharmacokinetics of a Double Prodrug of Ganiclovir in the Rat and Monkey", Drug Metabolism and Disposition, 23(11):1242-1247 (1995).
Krasny et al., "Allopurinol as an Inhibitor of the in vivo Formation of Acyclovir from Desiclovir", Biochem. Pharm., 35(23):4339-4340 (1986).
Krenitsky et al., "6-Deoxyacyclovir: A xanthjne oxidase-activated prodrug of acyclovir", Proc. Natl. Acad. Sci., 81:3209-3213 (1984).
Krenitsky et al., "Xanthine Oxidase from Human Liver: Purification and Characterization", Archives of Biochemistry and Biophysics, 247(1):108-119 (1986).
Kurimoto et al., "Prodrugs of 9-Benzyl-8-hydroxy-2-(2-hydroxyethylthio)adenine: Potent Interferon Inducing Agents in Monkeys", Chem. Pharm. Bull., 2004, 52(4):466-469.
Kurimoto et al., "Synthesis and evaluation of 2-substituted 8-hydroxyadenines as potent inferferon inducers with improved oral bioavailabilities", Bioorg. Med. Chem., 2004, 12:1091-1099.
Le Quesne et al., "Biomimetic Synthesis of Catechol Estrogens" Potentially Mutagenic Arene Oxide Intermediates in Estrogen Metabolism, J. Med. Chem, 1980, 23:239-240.
Lee et al., "Molecular basis for the immunostimulatory activity of guanine nucleoside analogs: activation of Toll-like receptor 7", PNAS, 2003, 100(11): 6646-6651.
Lewis et al., "Thiazolo[4,5-d]pyrimidines. Part I. Synthesis and Anti-Human Cytomegalovirus (HCMV) Activity in vitro of Certain Alkyl Derivatives", J. Het. Chem., 32, 547-56, 1995.

Lore et al, "Toll-Like Receptor Ligands Modulate Dendritic Cells to Augment Cytomegalovirus-and HIV-1-Specific T Cell Responses", *J. Immunol.*, 2003, 171(8): 4320-4328, abstract.

Mealy, "ANA-971", *Drugs of the Future*, 2004, 29(5):507.

Mealy, "ISIS-14803—20-Mer antisense phosphorothioate oligodeoxynucleotide whose sequence is: 5'GTGCmTCmATG-GTGCmACmGGTCmT-3' where Cm represents 5-methylcytidine", *Drugs of the Future*, May 2004, 29(5):526-27.

Michael et al, "Alkylpurines as Immunopotentiating Agents. Synthesis and Antiviral Activity of Certain Alkylguanines", *J. Med. Chem.*, 1993, 36:3431-3436.

Miettinen et al., "IFNs activate toll-like receptor gene expression in viral infections", *Genes Immun.*, 2001, 2(6):349-355.

Mohty et al., "IFN-α Skews Monocyte Differentiation into Toll-Like Receptor 7-Expressing Dendritic Cells with Potent Functional Activities", *J. Immunol.*, 2003, 171(7):3385-93.

Nagahara et al., "Thiazolo[4,5-d] pyrimidine Nucleosides. The Synthesis of Certain 3-B-D-Ribofuranosylthiazolo[4,5-d]pyrimidines as Potential Immunotherapeutic Agents", J. Med. Chem., 33(1):407-415 (1990).

Nagase et al.,"Expression and Function of Toll-Like Receptors in Eosinophils: Activation by Toll-Like Receptor 7 Ligand[1]", *J. Immunol.*, 2003, 171(8):3977-3982.

O'Neill, "After the Toll Rush", *Science*, 2004, 303:1481-1482.

Okada et al., "Murine thymic plasmacytoid dendritic cells", *Eur. J. Immunol.*, 2003, 33(4):1012-9.

Pinhal-Enfield et al., "An Angiogenic Switch in Macrophages Involving Synergy between Toll-Like Receptors 2, 4, 7, and 9 and Adenosine $A_{2A}$ Receptors", *Am. J. Pathol.*, 2003, 163(2):711-721.

Pockros et al., "A Phase IIa Placeob-Controlled, Double-Blind Trial to Determine the Safety, Tolerability, PK/PD of An Oral Interferon Inducer, Resiquimod, in chronic HCV", *Gastroenterology*, 2003, 124(Suppl 1): A-766.

Pockros, "Attacking the Hepatitis C Virus with New Mechanisms of Action: Drugs in the Pipeline", *The HCV Advocate: Medical Writer's Circle*, May 2004, pp. 1-5.

Purifoy et al., "Review of Research Leading to New Anti-Herpesvirus Agents in Clinical Development: Valaciclovir Hydrochloride (256U, the L-Valyl Ester of Acyclovir) and 882C, a Specific Agent for Varicella Zoster Virus", Journal of Medical Virology Supplement, 1:139-145 (1993).

Raney et al, "HEP DART 2003: Frontiers in Drug Development for Viral Hepatitis", *Expert Opin. Investig. Drugs*, 2004, 13(3):289-293.

Reitz, et al., "Small-Molecule Immunostimulants. Synthesis and Activity of 7,8-Disubstituted Guasnosines and Structurally Related Compounds", *J. Med. Chem.*, 1994, 37(21):3561-3578.

Revankar et al., "Synthesis and Antiviral/Antitumor Activities of Certain 3-Deazaguanine Nucleosides and Nucleotides", *J. Med. Chem.*, 1984, 27:1389-96.

Revankar et al., "Thiazolo[4,5-d]Pyrimidines. Part II. Synthesis and Anti-human Cytomegalovirus Activity in Vitro of Certain Acyclonucleosides and Acyclonucleotides Derived from Guanine Analogue 5-Aminothiazolo[4,5-d]Pyrimidine-2,7(3H,6H)-dione", Antiviral Chemistry & Chemotherapy, 9:53-63 (1998).

Revankar et al., "Synthesis of Certain *N*- and *C*-Alkyl Purine Analogs", J. Het. Chem., 30, 1341-49 (1993).

Rhodes, "Discovery of immunopotentiatory drugs: current and future strategies", *Clin. Exp. Immunol.*, 2002, 130:363-369.

Rida et al., "Synthesis of Novel Thiazolo[4,5-d]Pyrimidine Derivatives for Antimicrobial, Anti-HIV and Anticancer Investigation", Pharmazie, 51(12):927-931 (1996).

Rothenfusser et al., "Plasmacytoid Dendritic Cells: The Key to CpG", *Hum. Immunol.*, 2002, 63(12):1111-1119.

Sato et al., "A variety of microbial components induce tolerance to lipopolysaccharide by differentially affecting MyD88-dependent and -independent pathways", *Int. Immunol.*, 2002, 14(7):783-91.

Seela et al., :Alternative d(G-C)3 and d(C-G)3 Hexanucleotides Containing 7-Deaza-2'-deoxyguanosine or 8-Aza-7-deaza-2'-deoxyguanosine in Place of dG, Nucleic Acids Res., 17(3):901-910 (1989).

Seela et al., "Synthese von 2-Amino-2,7-dihydro-7-(β-D-ribofuranosyl)-4H-pyrrolo[2,3-*d*]pyrimidin-4-on—7-Desazaguanosin—der Stammverbindung des Nucleosids Q", *Chem. Ber.*, 1981, 114 (10):3395-3402.

Skulnick et al., "Pyrimidinones. 3. N-Substituted 6-Phenylpyrimidinones and Pyrimidinediones with Diuretic/Hypotensive and Antiinflammatory Activity", *J. Med. Chem.*, 1986, 29:1499-1504.

Smee et al., "Broad Spectrum In Vivo Antiviral Activity of 7-Thia-8-Oxoguanoine, a Novel Immunopotentiating Agent", Antimicrobial Agents and Chemotherapy, 33(9):1487-1492 (1989).

Smee et al., "Broad-Spectrum Activity of 8-chloro-7-deazaguanosine Against RNA Virus Infections in Mice and Rats", Antiviral Res., 26:203-209 (1995).

Townsend, "The Synthesis of 2-Amiono-7-β-D-ribofuranosyl)pyrrolo[2,3,d)-pyrimidin-4-one (7-Deazaguanosine), a Nucleoside Q and Q* Analog (1)", *J. Heterocyclic Chem*, Dec. 1976, 13:1363-1364.

Ulevitch, "Therapeutics Targeting the Innate Immune System", *Nature*, 2004, 4:512-520.

Wong et al., "Photochemical Synthesis of 8-Hydroxyguanine Nucleosides", Methods Enzymol., 234:59-65 (1994).

Yamamoto et al., "Cutting Edge: A Novel Toll/IL-1 Receptor Domain-Containing Adapter That Preferentially Activates the IFN-β Promoter in the Toll-Like Receptor Signalinig[1]", *J. Immunol.*, 2002, 169(12):6668-72.

Yamamoto et al., "Essential role for TIRAP in activation of signaling cascade shared by TLR2 and TLR4", *Nature*, 2002, 420(6913):324-9.

"Oral Interferon-Like Molecule", *Updated on New Experimental Therapies*, <http://archive.mail-list.com/pkids/msg03975.html>, Jul. 21, 2004.

International Search Report and Written Opinion (PCT/US05/45589) dated May 18, 2006.

International Search Report and Written Opinion (PCT/US2007/21830) dated Jun. 23, 2008.

Narayan C. Chaudhuri, "Convenient Strategies for the Preparation of Modified 2(3*H*)-Benzothiazolethiones", Synthetic Communications, 26(20), 3783-3790 (1996).

Baldev Singh et al., "An Efficient and Novel Synthesis of Fused thiasol-2(3*H*)-Ones", Heterocycles, vol. 36, No. 1, 1992.

Baldev Singh et al., "Novel cAMP PDE III Inhibitors: Imidazo[4,5-*b*]pyridin-2(3*H*)-ones and Thiazolo[4,5-*b*]pyridin-2(3*H*)-ones and Their Analogs", J. Med. Chem. 1994, 37, 248-254.

Baldev Singh et al., Novel and Potent Adenosine 3',5'-Cyclic Phosphate Phosphodiesterase III Inhibitors: Thiazolo[4,5-*b*][1,6]naphthyridin-2-ones, J. Med. Chem, 1995, 38, 2546-2550.

\* cited by examiner

PROCESS FOR THE PREPARATION OF 5-AMINO-3H-THIAZOLO[4,5-D]PYRIMIDIN-2-ONE

CROSS REFERENCE TO RELATED APPLICATION

This nonprovisional application claims priority under 35 U.S.C. §119(e) on U.S. Provisional Application No(s). 60/738,055 filed on Nov. 21, 2005, the entire contents of which are hereby incorporated by reference.

FIELD OF THE INVENTION

The present invention relates to a process for the preparation of the title compound, 5-amino-3H-thiazolo[4,5-d]pyrimidin-2-one, which is a useful intermediate in the preparation of certain thiazolo[4,5-d]pyrimidine nucleosides, which can have utility as immunomodulators.

BACKGROUND

A variety of D- and L-purine nucleoside analogs have been explored for use as immunomodulators. A class of nucleoside analogs that can have utility for such purpose are thiazolo[4,5-d]pyrimidine nucleosides, such as those compounds disclosed in United States Published Application No. 2005/0070556, assigned to Anadys Pharmaceuticals, Inc., the entire disclosure of which is incorporated herein by reference. These compounds include, for example, 5-Amino-3-β-D-ribofuranosyl-3H-thiazolo[4,5-d]pyrimidin-2-one of formula

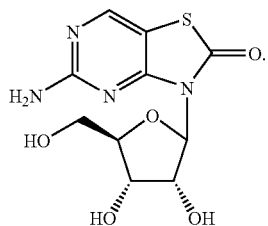

A useful intermediate in the preparation of this and other thiazolo[4,5-d]pyrimidine nucleosides is the pyrimidine base, 5-amino-3H-thiazolo[4,5-d]pyrimidin-2-one of formula

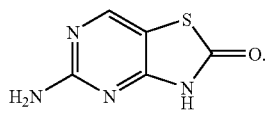

It would be desirable to provide an efficient and cost-effective process for the preparation of this compound. The present invention provides such a process.

SUMMARY OF THE INVENTION

The invention is directed to a process for the preparation of 5-amino-3H-thiazolo[4,5-d]pyrimidin-2-one. The process comprises:

(i) halogenating a 2,4-diaminopyrimidine of formula

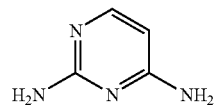

to form a 2,4-diamino-5-halo-pyrimidine of formula

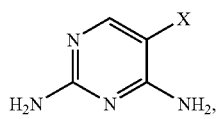

wherein X represents halo selected from F, Cl, Br, and I;

(ii) cyclocondensing the 2,4-diamino-5-halo-pyrimidine to form 5-amino-3H-thiazolo[4,5-d]pyrimidin-2-thione of formula

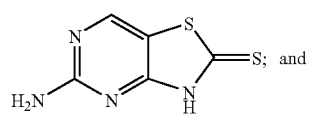

(iii) oxidizing the 5-amino-3H-thiazolo[4,5-d]pyrimidin-2-thione to form 5-amino-3H-thiazolo[4,5-d]pyrimidin-2-one.

In one embodiment, the invention is directed to a process for cyclocondensing a 2,4-diamino-5-halo-pyrimidine of formula

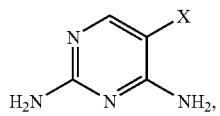

wherein X is halo selected from F, Cl, Br, and I, to form 5-amino-3H-thiazolo[4,5-d]pyrimidin-2-thione, wherein the cyclocondensation is carried out in the presence of a xanthogenate compound having the formula

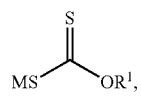

wherein M is a metal cation and $R^1$ is an alkyl group; and wherein the reaction comprises heating the above reactants under nitrogen in the presence of an inert solvent.

In another embodiment, the invention is directed to a process for oxidizing 5-amino-3H-thiazolo[4,5-d]pyrimidin-2-thione to form 5-amino-3H-thiazolo[4,5-d]pyrimidin-2-one, wherein the process comprises reacting 5-amino-3H-thiazolo[4,5-d]pyrimidin-2-thione with an oxidizing agent under basic conditions and a subsequent acidic hydrolysis to give the desired 5-amino-3H-thiazolo[4,5-d]pyrimidin-2-one.

DETAILED DESCRIPTION OF THE INVENTION

The present invention provides a novel process for the manufacture and purification of 5-amino-3H-thiazolo[4,5-d]pyrimidin-2-one, a useful intermediate in the preparation of thiazolo[4,5-d]pyrimidine nucleosides, such as 5-amino-3-β-D-ribofuranosyl-3H-thiazolo[4,5-d]pyrimidin-2-one. The process involves the conversion of 2,4-diaminopyrimidine to 2,4-diamino-5-halo-pyrimidine followed by a cyclocondensation to afford 5-amino-3H-thiazolo[4,5-d]pyrimidin-2-thione, and subsequent oxidation to the title compound.

The process can be made to be operationally simple, efficient, and robust, resulting in high overall yield and high throughput. For example, the three-step process of the invention can result in a yield of over 50%. In addition, the process can be made to be environmentally friendly, with low overall amounts of waste materials. Moreover, the process involves the use of inexpensive reagents, can be practiced without the use of chromatography, and can be amendable to scale-up. In this regard, the starting material for the process, 2,4-diaminopyrimidine, is relatively inexpensive and is commercially available in bulk quantities.

As used herein, the term "halogen" refers to fluorine, chlorine, bromine, and iodine and the term "halo" refers to substituents of the same.

As used herein, the term "alkyl" includes saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms. Particularly notable alkyl groups include methyl, ethyl, propyl, and butyl.

The compounds of the invention may exhibit the phenomenon of tautomerism. While each formula drawing provided cannot expressly depict all possible tautomeric forms, it is to be understood that each formula is intended to represent any tautomeric form of the depicted compound and are not to be limited merely to a specific compound form depicted by the formula drawings. For example (as shown below), it is understood for the below formula that regardless of whether or not the substituents are shown in their enol or their keto form, they represent the same compound.

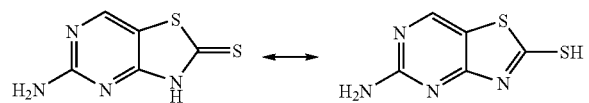

As used herein, the term "metal cation" refers to a cationic metal ion. Particularly notable metal cations are those of group 1A of the periodic table, including cations of lithium (Li), sodium (Na), and potassium (K).

As used herein, the term "inert solvent" refers to any solvent that can dissolve but will not significantly react with the reactants of a given reaction or reaction system. For example, in the cyclocondensation 2,4-diamino-5-halo-pyrimidine to form
5-amino-3H-thiazolo[4,5-d]pyrimidin-2-thione, suitable inert solvents can, for example, include N,N-Dimethylformamide (DMF), N,N-Dimethylacetamide (DMAc) and N-methyl pyrolidinone (NMP).

As used herein, the term "oxidizing agent" refers to a substance or species that gains electrons in a chemical reaction. For example, in the oxidation of 5-amino-3H-thiazolo[4,5-d]pyrimidin-2-thione to form 5-amino-3H-thiazolo[4,5-d]pyrimidin-2-one, suitable oxidizing agents can, for example, include hydrogen peroxide ($H_2O_2$), urea, hydrogen peroxide ($NH_2CONH_2.H_2O_2$), and sodium hypochlorite (NaClO).

The first step of a process falling within the scope of the invention involves halogenation of 2,4-diaminopyrimidine to form 2,4-diamino-5-halo-pyrimidine. This step can, for example, be carried out by first dissolving 2,4-diaminopyrimidine in a suitable solvent and then introducing a halogenating agent to the reaction mixture.

The temperature of reaction mixture in this step can, for example, range from about −20° C. to 50° C., such as from about 0° C. to room temperature (about 25° C.). In addition, the molar ratio of 2,4-diaminopyrimidine to halogenating agent can, for example, range from about 1.0:1.5 to 1.0:1.0, such as about 1.0:1.1 to 1.0:1.0. The volume of solvent per gram of 2,4-diaminopyrimidine can, for example, range from about 5 ml to 100 ml, such as about 10 ml to 30 ml.

Examples of suitable solvents include tetrahydrofuran (THF), acetonitrile, methanol, ethanol, water and acetic acid. Preferred solvents include THF and acetic acid. Examples of halogenating agents include $Br_2$, $Cl_2$, $F_2$, $I_2$, and pyridinium tribromide ($PyHBr_3$). Preferred halogenating agents include $Br_2$ and $PyHBr_3$. When $Br_2$ or $PyHBr_3$ are used as halogenating agents, the compound produced in this first step is 2,4-diamino-5-bromo-pyrimidine.

The reaction product from this first step can be separated from the reaction mixture by any means known to those skilled in the art. For example, the reaction product can be separated from the reaction mixture by filtration, neutralization, filtration and washing with a solvent (for example, water) and/or a combination of these.

Alternately, the reaction product from this first step can be neutralized, concentrated and carried on to the next step without isolation.

Other methods of halogenating substituted pyrimidine compounds have been disclosed in, for example, English et al., *J Am. Chem. Soc'y*, 68, 453-58 (1946).

The next step of a process falling within the scope of the invention involves cyclocondensation 2,4-diamino-5-halo-pyrimidine to form 5-amino-3H-thiazolo[4,5-d]pyrimidin-2-thione. This step can, for example, be carried out by reacting a 2,4-diamino-5-halo-pyrimidine, such as 2,4-diamino-5-bromo-pyrimidine, with a xanthogenate compound having the general formula:

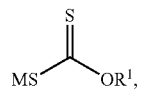

wherein M represents a metal cation and $R^1$ is an alkyl group. Such a reaction can, for example, be carried out by dissolving both reagents in an inert solvent, with heating, under $N_2$ for a specified period of time.

The temperature of reaction solution in this step can, for example, range from about 50° C. to 200° C. In another embodiment, the temperature range for this step is about 130° C. to 180° C. In addition, the molar ratio of 2,4-diamino-5-halo-pyrimidine to the xanthogenate compound can, for example, range from about 1:10 to 1:1, such as from about 1:2 to 1:1. The volume of solvent per gram of 2,4-diamino-5-halo-pyrimidine can, for example, range from about 5 ml to 100 ml, such as about 10 ml to 40 ml.

Examples of suitable inert solvents include DMF, NMP, DMAc (Dimethylacetamide), DMSO (Dimethylsulfoxide), Dimethylsulfone and Sufolane(tetramethylene sulfone).

With regard to the xanthogenate compound, examples of suitable metal cations include potassium and sodium. Examples of alkyl groups include methyl and ethyl. A preferred xanthogenate compound is potassium ethyl xanthogenate.

The reaction product from this step can be separated from the reaction mixture by any means known to those skilled in the art. For example, the reaction product can be separated from the reaction mixture by addition of water, neutralization, filtration, washing with a solvent (for example, water and/or ethanol), and/or a combination of these.

The next step of a process falling within the scope of the invention involves oxidation of 5-amino-3H-thiazolo[4,5-d]pyrimidin-2-thione to form the title compound, 5-amino-3H-thiazolo[4,5-d]pyrimidin-2-one. This step can, for example, be carried out by reacting 5-amino-3H-thiazolo[4,5-d]pyrimidin-2-thione with an oxidizing agent under basic conditions, and a subsequent acidic hydrolysis.

The temperature of the reaction solution in this step can, for example, range from about 0° C. to 100° C. In another embodiment, the temperature ranges from about 20° C. to 90° C.

In addition, the molar ratio of 5-amino-3H-thiazolo[4,5-d]pyrimidin-2-thione to oxidizing agent can, for example, range from about 1:5 to 1:1, such as from about 1:3 to 1:2. The volume of solvent per gram of 5-amino-3H-thiazolo[4,5-d]pyrimidin-2-thione can, for example, range from about 5 ml to 100 ml, such as from about 10 ml to 30 ml.

In at least one embodiment of the invention, the basic conditions under which 5-amino-3H-thiazolo[4,5-d]pyrimidin-2-thione is reacted with an oxidizing agent can be provided by first dissolving a base, such as an inorganic base, in water followed by adding 5-amino-3H-thiazolo[4,5-d]pyrimidin-2-thione to the resulting solution. An oxidizing agent can then be added to the solution. The molar ratio of base to 5-amino-3H-thiazolo[4,5-d]pyrimidin-2-thione can, for example, range from about 1:5 to 1:1, such as from about 1:3 to 1:1.

Examples of bases that can be used include but not limited to inorganic bases, such as NaOH and KOH. Examples of oxidizing agents include but not limited to hydrogen peroxide, urea hydrogen peroxide, and sodium hypochlorite. Acids that can be used in the hydrolysis include any suitable acid, for example, HCl (including concentrated HCl).

The reaction product from this step, which is the title compound, can be separated from the reaction mixture by any means known to those skilled in the art. For example, the reaction product can be separated from the reaction mixture by filtration, neutralization with base, filtration and washing with a solvent (for example, water and/or acetonitrile), and/or a combination of these.

In one embodiment of the invention the title compound can be made without the use of chromatography separation or purification for each of the three individual process steps.

The following non-limiting examples illustrate the present invention.

Preparation of Compounds

In the examples described below, unless otherwise indicated all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF) and N,N-dimethylformamide (DMF) were purchased from Aldrich in Sure Seal bottles and used as received.

The reactions set forth below were done generally under a positive pressure of argon or nitrogen at an ambient temperature (unless otherwise stated) in anhydrous solvents. The reactions were assayed by TLC and/or analyzed by LC-MS and terminated as judged by the consumption of starting material. Analytical thin layer chromatography (TLC) was performed on glass-backed silica gel 60 $F_{254}$ 0.2 mm plates (EM Science), and visualized with UV light (254 nm) followed by heat.

$^1$H-NMR spectra and $^{13}$C-NMR were recorded on a Varian Mercury-VX400 instrument operating at 400 MHz. NMR spectra were obtained as $CDCl_3$ solutions (reported in ppm), using chloroform as the reference standard (7.27 ppm and 77.00 ppm), $CD_3OD$ (3.4 and 4.8 ppm and 49.3 ppm), DMSO-$d_6$, or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Mass spectra reported are (+)-ES or APCI(+)LC/MS conducted by the Analytical Chemistry Department of Anadys Pharmaceuticals, Inc.

The described synthetic pathways and experimental procedures utilize many common chemical abbreviations, THF (tetrahydrofuran), DMF (N,N-dimethylformamide), EtOAc (ethyl acetate), DMSO (dimethyl sulfoxide), MeCN (acetonitrile), MeOH (methanol), HPLC (high pressure liquid chromatography), TLC (thin layer chromatography), $Br_2$ (bromine), $H_2O_2$ (hydrogen peroxide) and the like.

Example 1

Step 1: Halogenation to
2,4-diamino-5-bromo-pyrimidine

To a stirring mixture of 2,4-diaminopyrimidine (25 g, 0.23 mol, 1.0 eq) in acetic acid (375 ml) was added $Br_2$ (36.3 g, 0.23 mol, 1.0 eq) at room temperature. The resulting mixture was stirred at room temperature (about 25° C.) for 2 hours and then filtered. The yellow solid was mixed with water (250 ml) and the pH of the resulting mixture was adjusted to 8-9 using 50% NaOH solution. Stirring was continued at room temperature for 30 min and the mixture was filtered, washed with water, and then dried under vacuum to give 38 g (87%) of 2,4-diamino-5-bromo-pyrimidine as a white solid. $^1$H NMR (400 MHz, $d_6$-DMSO) δ 6.06 (s, 2H, ex. $D_2O$), 6.50 (br, 2H, ex. $D_2O$), 7.76 (s, 1H); MS (+)-ES [M+H]$^+$ m/z 191.

Step 2: Cyclocondensation to
5-amino-3H-thiazolo[4,5-d]pyrimidin-2-thione

A solution of 2,4-diamino-5-bromo-pyrimidine (9.5 g, 50 mmol, 1.0 eq) and potassium ethyl xanthogenate (16 g, 100 mmol. 2 eq) in DMF (300 ml) was heated up to reflux for 10 hours under $N_2$. The reaction solution was cooled down to room temperature and water (600 ml) was added. The pH of the solution was then adjusted to about 5 using $H_2SO_4$ (2 ml) and the resulting suspension was stirred at 50-60° C. for 30 min., cooled to about 30° C., filtered and washed with water. The product was dried under vacuum at 50-60° C. to give 8.2 g (89%) of 5-amino-3H-thiazolo[4,5-d]pyrimidin-2-thione as a yellow solid. $^1$H NMR (400 MHz, d$_6$-DMSO). δ 6.91 (s, 2H, ex. D$_2$O), 8.34 (s, 1H), 12.3 (br, 1H, ex. D$_2$O); MS (+)-ES [M+H]$^+$ m/z 185.

Step 3: Oxidation to 5-amino-3H-thiazolo[4,5-d]pyrimidin-2-one

Procedure A: To a solution of NaOH (0.6 g, 15 mmol, 3 eq) in water (20 ml) was added 5-amino-3H-thiazolo[4,5-d]pyrimidin-2-thione (0.92 g, 5 mmol, 1.0 eq). The mixture was stirred to dissolve. An aqueous solution of H$_2$O$_2$ (0.68 g, 2.3 ml (30%), 20 mmol, 4 eq) was slowly added dropwise to the above solution, keeping the temperature below 50° C. The reaction was then cooled down to room temperature (about 25° C.). Concentrated HCl (37%, 6 ml) was added to the above solution until the pH is less than 1. The mixture is stirred at room temperature for 30 minutes. Celite (2 g) was added to the suspension and the suspension was filtered and washed with water (10 ml). To the filtrate was added 50% NaOH solution to adjust the pH to 5-5.5, stirred for 30 minutes, filtered, washed with water, and dried at 50° C. under vacuum to give 0.52 g (62%) of 5-amino-3H-thiazolo[4,5-d]pyrimidin-2-one as a pale yellow solid. $^1$H NMR (400 MHz, d$_6$-DMSO) δ 6.70 (s, 2H, ex. D$_2$O), 8.2 (s, 1H), 12.2 (br s, 1H, ex. D$_2$O); MS (+)-ES [M+H]$^+$ m/z 169.

Alternately, the procedure for Step 3 can be done using urea hydrogen peroxide instead of hydrogen peroxide:

Procedure B: To a solution of NaOH (0.6 g, 15 mmol, 3 eq) in water (20 ml) was added 5-amino-3H-thiazolo[4,5-d]pyrimidin-2-thione (0.92 g, 5 mmol, 1.0 eq). The mixture was stirred to dissolve. Urea hydrogen peroxide (2.8 g, 30 mmol, 6 eq) was slowly added dropwise to the above solution, keeping the temperature below 50° C. The reaction was then cooled down to room temperature (about 25° C.). Concentrated HCl (37%, 6 ml) was added to the above solution until the pH is less than 1. The mixture is stirred at room temperature for 30 minutes. Celite (2 g) was added to the solution and the solution was filtered and washed with water (10 ml). To the filtrate was added 50% NaOH solution to adjust the pH to 5-5.5. The solution was heated up to 50-60° C. for 30 minutes. The resulting solution was cooled down to room temperature, filtered, and washed with water, dried at 50° C. under vacuum to give 0.56 g (67%) of 5-amino-3H-thiazolo[4,5-d]pyrimidin-2-one as a pale yellow solid. $^1$H NMR, HPLC and LCMS analyses of this product are identical to the product described from Procedure A in Step 2 of Example 1 above.

Example 2

Step 1: Halogenation to 2,4-diamino-5-bromo-pyrimidine

To a mixture of 2,4-diaminopyrimidine (5.5 g, 0.05 mol, 1.0 eq.) and THF (200 ml) was added pyridinium tribromide (17.5 g, 0.055 mol, 1.1 eq) at 0° C. in three portions. The resulting mixture was stirred at about 0° C. for two hours, filtered and washed with THF (20 ml). The yellow solid was mixed with water (100 ml) and the resulting mixture was neutralized with 10% NaOH solution to a pH of about 7. Stirring was continued at room temperature for 30 minutes, after which the mixture was filtered, washed with water (2×20 ml) and dried under vacuum at 50° C. to give 8.2 g (87%) of 2,4-diamino-5-bromo-pyrimidine as a white solid. $^1$H NMR, HPLC and LCMS analyses of this product are identical to the product described in Step 1 of Example 1.

Step 2: Cyclocondensation to 5-amino-3H-thiazolo[4,5-d]pyrimidin-2-thione

A solution of 2,4-diamino-5-bromo-pyrimidine (0.95 g, 5 mmol, 1.0 eq) and potassium ethyl xanthogenate (1.6 g, 10 mmol. 2.0 eq) in DMF (30 ml) heated up to reflux for 10 hours under N$_2$. The reaction solution was cooled down to room temperature (about 25° C.) and water (30 ml) was added to the solution. The pH of the solution was adjusted to about 5 with 3.6 N H$_2$SO$_4$. The resulting mixture was heated up to 50-60° C. for 1 hour, cooled to room temperature stirred for 2 hours, filtered, washed with water (20 ml) and ethanol (20 ml) and dried to give 0.8 g (87%) of 5-amino-3H-thiazolo[4,5-d]pyrimidin-2-thione as a yellow solid. $^1$H NMR, HPLC and LCMS analyses of this product are identical to the product described in Step 2 of Example 1.

Step 3: Oxidation to 5-amino-3H-thiazolo[4,5-d]pyrimidin-2-one

5-Amino-3H-thiazolo[4,5-d]pyrimidin-2-thione (0.24 g, 1.3 mmol, 1.0 eq) was dissolved in 8 ml water containing 0.1 g NaOH (2.5 mmol, 2.5 eq). The resulting solution was heated to 80° C. A solution of sodium hypochlorite (NaClO) (4.4 ml, 10-13% solution, 5 eq) was added slowly to the above solution at about 80° C. and stirring was continued at 80-90° C. for 30 minutes. The solution was cooled down to about 70° C. and a concentrated HCl solution (0.3 ml, 37%, 2.3 eq.) was added, after which the resulting solution was heated to 80-90° C. for one hour. The reaction mixture was cooled down to room temperature and filtered through a pad of celite. The pH of the filtrate was adjusted to 5-5.5 using 10% NaOH solution. The resulting mixture was heated up to 60° C. for 1 hour, cooled to room temperature and stirred for at least two hours, filtered and washed with water and acetonitrile to afford 0.06 g (27%) of 5-amino-3H-thiazolo[4,5-d]pyrimidin-2-one as a pale yellow solid. $^1$H NMR, HPLC and LCMS analyses of this product are identical to the product described in Step 3 of Example 1.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

What is claimed is:

1. A process for the preparation of 5-amino-3H-thiazolo[4,5-d]pyrimidin-2-one of formula

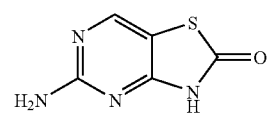

comprising:
(i) halogenating a 2,4-diaminopyrimidine of formula

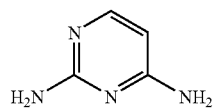

to form 2,4-diamino-5-halo-pyrimidine of formula

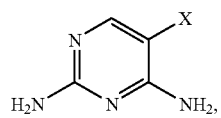

wherein X represents halo selected from F, Cl, Br, and I;
(ii) cyclocondensing the 2,4-diamino-5-halo-pyrimidine to form 5-amino-3H-thiazolo[4,5-d]pyrimidin-2-thione of formula

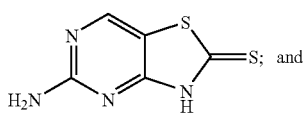

(iii) oxidizing the 5-amino-3H-thiazolo[4,5-d]pyrimidin-2-thione to form 5-amino-3H-thiazolo[4,5-d]pyrimidin-2-one.

2. The process of claim 1, wherein X is selected from Br and Cl.

3. The process of claim 2, wherein X is Br.

4. The process of claim 1, wherein the cyclocondensation step is carried out in the presence of a xanthogenate compound having the formula:

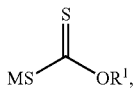

wherein M represents a metal cation and $R^1$ is an alkyl group.

5. The process of claim 4, wherein M is selected from a potassium cation and a sodium cation and $R^1$ is selected from a methyl group and an ethyl group.

6. The process of claim 5, wherein M is a potassium cation and $R^1$ is an ethyl group.

7. The process of claim 1, wherein the oxidizing step comprises reacting 5-amino-3H-thiazolo[4,5-d]pyrimidin-2-thione with an oxidizing agent under basic conditions and a subsequent acidic hydrolysis.

8. The process of claim 7, wherein the oxidizing agent is selected from hydrogen peroxide, urea hydrogen peroxide, and sodium hypochlorite.

9. The process of claim 8, wherein the oxidizing agent is hydrogen peroxide.

10. The process of claim 4, wherein X is selected from Cl and Br, M is selected from a potassium cation and a sodium cation, $R^1$ is selected from a methyl group and an ethyl group, and the oxidation step comprises reacting 5-amino-3H-thiazolo[4,5-d]pyrimidin-2-thione with an oxidizing agent under basic conditions and a subsequent acidic hydrolysis.

11. The process of claim 10, wherein X is Br, M is a potassium cation, $R^1$ is an ethyl group, and the oxidizing agent is hydrogen peroxide.

12. A process for cyclocondensing 2,4-diamino-5-halo-pyrimidine of formula:

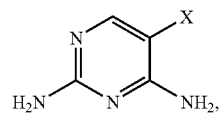

wherein X is halo selected from F, Cl, Br, and I;
to form 5-amino-3H-thiazolo[4,5-d]pyrimidin-2-thione of formula

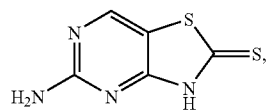

wherein the cyclocondensation is carried out in the presence of a xanthogenate compound having the formula

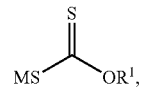

wherein M is a metal cation and $R^1$ is an alkyl group; and
wherein the reaction comprises heating up the solution of above reactants in the presence of an inert solvent.

13. The process of claim 12, wherein X is selected from Br or Cl, M is selected from a potassium cation and a sodium cation, $R^1$ is selected from a methyl group and an ethyl group, and the inert solvent is selected from N,N-Dimethylformamide (DMF) and N-methyl pyrrolidinone (NMP).

14. The process of claim 13, wherein X is Br, M is a potassium cation, $R^1$ is an ethyl group, and the inert solvent is DMF.

15. The process of claim 12, wherein the molar ratio of 2,4-diamino-5-halo-pyrimidine to the xanthogenate compound ranges from about 1:10 to 1:1, the temperature ranges from about 50° C. to 200° C., and the volume of inert solvent per gram of 2,4-diamino-5-halo-pyrimidine ranges from about 5 ml to 100 ml.

16. The process of claim 15, wherein the molar ratio of 2,4-diamino-5-halo-pyrimidine to the xanthogenate compound ranges from about 1:2 to 1:1, the temperature ranges from about 140° C. to 165° C., and the volume of inert solvent per gram of 2,4-diamino-5-halo-pyrimidine ranges from about 10 ml to 40 ml.

* * * * *